(12) United States Patent
Gupta

(10) Patent No.: US 9,974,925 B2
(45) Date of Patent: May 22, 2018

(54) CATHETER SHAFT CONSTRUCTIONS HAVING CONTRAST FLUID LUMEN

(71) Applicant: BOSTON SCIENTIFIC SCIMED, INC., Maple Grove, MN (US)

(72) Inventor: Ajay Gupta, Little Canada, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 855 days.

(21) Appl. No.: 14/192,666

(22) Filed: Feb. 27, 2014

(65) Prior Publication Data

US 2014/0276043 A1  Sep. 18, 2014

Related U.S. Application Data

(60) Provisional application No. 61/777,826, filed on Mar. 12, 2013.

(51) Int. Cl.
| | |
|---|---|
| A61M 25/00 | (2006.01) |
| B29C 65/00 | (2006.01) |
| A61M 31/00 | (2006.01) |
| B29L 31/00 | (2006.01) |
| B29C 65/16 | (2006.01) |
| B29C 65/48 | (2006.01) |
| B29C 65/02 | (2006.01) |

(52) U.S. Cl.
CPC ...... *A61M 25/003* (2013.01); *A61M 25/0009* (2013.01); *A61M 25/0032* (2013.01); *A61M 31/005* (2013.01); *A61M 2025/0034* (2013.01); *B29C 65/02* (2013.01); *B29C 65/16* (2013.01); *B29C 65/48* (2013.01); *B29C 66/1122* (2013.01); *B29C 66/5221* (2013.01); *B29C 66/5344* (2013.01); *B29C 66/53241* (2013.01); *B29C 66/63* (2013.01); *B29L 2031/7542* (2013.01); *B29L 2031/7543* (2013.01)

(58) Field of Classification Search
CPC .............. A61M 25/003; A61M 31/005; B29L 2031/7543
See application file for complete search history.

(56) References Cited

U.S. PATENT DOCUMENTS

| | | |
|---|---|---|
| RE31,873 E * | 4/1985 | Howes ............... A61B 5/02152 600/487 |
| 4,748,984 A | 6/1988 | Patel |
| 4,892,519 A | 1/1990 | Songer et al. |
| 4,909,258 A | 3/1990 | Kuntz et al. |

(Continued)

FOREIGN PATENT DOCUMENTS

WO  2007132447 A2  11/2007

*Primary Examiner* — Bradley J Osinski
(74) *Attorney, Agent, or Firm* — Seager, Tufte & Wickhem, LLP

(57) ABSTRACT

A balloon catheter including a dedicated contrast fluid lumen is disclosed. The contrast fluid lumen extends through the catheter shaft to a contrast fluid delivery port located proximate the inflatable balloon and is configured to deliver contrast fluid to a target location. The catheter shaft includes a joint located proximate the contrast fluid port formed between a distal end of a proximal outer tubular member, a distal end of an inner tubular member and a proximal end of a distal outer tubular member. A guidewire tube, defining a guidewire lumen, may extend through the lumen of the proximal and distal outer tubular members.

18 Claims, 11 Drawing Sheets

(56) References Cited

U.S. PATENT DOCUMENTS

| | | |
|---|---|---|
| 5,344,402 A | 9/1994 | Crocker |
| 5,759,191 A * | 6/1998 | Barbere .............. A61M 25/104 604/103.1 |
| 5,919,163 A | 7/1999 | Glickman |
| 6,322,577 B1 | 11/2001 | McInnes |
| 6,409,863 B1 | 6/2002 | Williams et al. |
| 6,733,486 B1 * | 5/2004 | Lee ................... A61M 25/0029 604/525 |
| 6,929,633 B2 | 8/2005 | Evan et al. |
| 8,109,985 B2 | 2/2012 | Meyer et al. |
| 2009/0036831 A1 | 2/2009 | Howat |
| 2011/0034949 A1 * | 2/2011 | Solar .................... A61M 25/10 606/194 |
| 2011/0137163 A1 | 6/2011 | Eder |
| 2011/0224708 A1 | 9/2011 | Sarradon |
| 2012/0259214 A1 | 10/2012 | Solar et al. |

* cited by examiner

CATHETER SHAFT CONSTRUCTIONS HAVING CONTRAST FLUID LUMEN

CROSS-REFERENCE TO RELATED APPLICATIONS

This application claims priority under 35 U.S.C. § 119 to U.S. Provisional Application Ser. No. 61/777,826, filed Mar. 12, 2013, the entirety of which is incorporated herein by reference.

TECHNICAL FIELD

This disclosure relates generally to medical devices for performing medical procedures. More particularly, the technologies disclosed herein relate to catheters and methods for constructing catheter shafts with a contrast fluid lumen.

BACKGROUND

A number of techniques have been developed to treat stenoses in coronary arteries or occlusions in blood vessels. One of these techniques, angioplasty, is a widely used technique. Angioplasty is a technique for dilating or reopening occluded blood vessels. A typical angioplasty device (also called the angioplasty catheter) includes the use of a guide catheter and a therapeutic device such as a balloon, located near the distal end of the angioplasty catheter. In many cases, the space between the angioplasty catheter and the guide catheter acts as a passage for contrast fluid to travel that exits at the distal end of the guide catheter. During operation, the distal end of the guide catheter is usually positioned in a blood vessel proximal of a stenosis. Then, the angioplasty catheter may be passed through a lumen in the guide catheter such that a balloon is positioned across a stenosis in the blood vessel. The balloon is then inflated for opening the stenosis in the blood vessel. At the time of inflating the balloon or thereafter, medical devices such as stents may also be placed. When the treatment is completed, the balloon is deflated and the angioplasty catheter is removed.

In such conventional medical devices, the cross-section of the guide catheter has to be large enough to create sufficient space between an outer surface of the angioplasty catheter and an inner surface of the guide catheter in order to allow easy flow of the contrast fluid. Also, the cross-section has to be large enough to hold the angioplasty catheter. In some instances, the guide catheter must be much larger than the balloon catheter to accommodate larger devices advanced through the guide catheter during the procedure. The large lumen between the guide catheter and the balloon catheter requires a large quantify of contrast fluid to fill the lumen. While performing medical procedures using conventional medical devices, more contrast fluid may be required to be delivered to a target site, e.g., the stenosis in a blood vessel, and this large volume of the contrast fluid may be deleterious for kidney function. In some instances, the contrast fluid may be delivered near a side branch away from the target site and may get distributed into branching vessels and the effectiveness of the contrast fluid is reduced. Additionally, in some instances the distal end of the guide catheter may be spaced proximally away from the target location in the anatomy such that the contrast fluid exits the guide catheter at a distance away from the target site, requiring the use of more contrast fluid to reach the target site. Furthermore, the large gap between the balloon catheter and the guide catheter may permit undesired blood flow up the guide catheter attributing to blood loss and/or the need for a sealing mechanism to inhibit blood loss.

Accordingly, it is desirable to provide alternative catheter devices and/or methods having improved mechanisms for treating occluded blood vessels, the heart, or other anatomical organs or structures.

SUMMARY

The disclosure is directed to several alternative designs, and methods of using medical device structures and assemblies for treating occluded blood vessels, the heart, or other anatomical organs or structures.

Accordingly, one illustrative embodiment is a catheter. The catheter includes a hub assembly, and a catheter shaft that extends distally from the hub assembly to a distal end. The catheter further includes an inflatable balloon mounted proximate the distal end of the catheter shaft. Further, the catheter includes an inflation lumen extending through the catheter shaft from the hub assembly to the inflatable balloon. Furthermore, the catheter includes a guidewire lumen extending through at least a portion of the catheter shaft. Moreover, the catheter includes a contrast fluid lumen extending through the catheter shaft to a contrast fluid delivery port located proximate the inflatable balloon, where the contrast fluid lumen is configured to deliver contrast fluid to a target location. Additionally, the catheter shaft includes an outer tubular member having a lumen extending through it, and a guidewire tube extending through the lumen of the outer tubular member. The inflation lumen is defined between an inner surface of the outer tubular member and an outer surface of the guidewire tube. The guidewire lumen is defined by the guidewire tube.

Another illustrative embodiment may include a catheter. The catheter includes a hub assembly, and a catheter shaft extending distally from the hub assembly. The catheter shaft includes a proximal outer tubular member, a distal outer tubular member, and an inner tubular member extending through the proximal outer tubular member, and a guidewire tube extending through the distal outer tubular member. The catheter further includes a therapeutic device that is mounted on a distal end region of the catheter shaft. The catheter further includes a contrast fluid delivery port located on the catheter shaft proximal of the therapeutic device and used for delivering a contrast fluid to a target location. A distal end of the proximal outer tubular member, a proximal end of the distal outer tubular member and a distal end of the inner tubular member are bonded together at a joint. Additionally, the contrast fluid delivery port is located proximate to the joint.

Additionally, an illustrative embodiment discloses a method for constructing a medical catheter. The method includes bonding an end of a proximal outer tubular member, an end of a distal outer tubular member and an end of an inner tubular member together at a joint such that a lumen of the proximal outer tubular member is in communication with a lumen of the distal outer tubular member. The method further includes forming a port at the joint in communication with a lumen of the inner tubular member. Additionally, the method includes positioning a guidewire tube across the joint such that a first portion of the guidewire tube is positioned within the lumen of the proximal outer tubular member and a second portion of the guidewire tube is positioned within the lumen of the distal outer tubular member.

The above summary of some example embodiments is not intended to describe each disclosed embodiment or every implementation of the present disclosure.

BRIEF DESCRIPTION OF THE DRAWINGS

The disclosure may be more completely understood in consideration of the following detailed description of various embodiments in connection with the accompanying drawings, in which.

Figure 1:
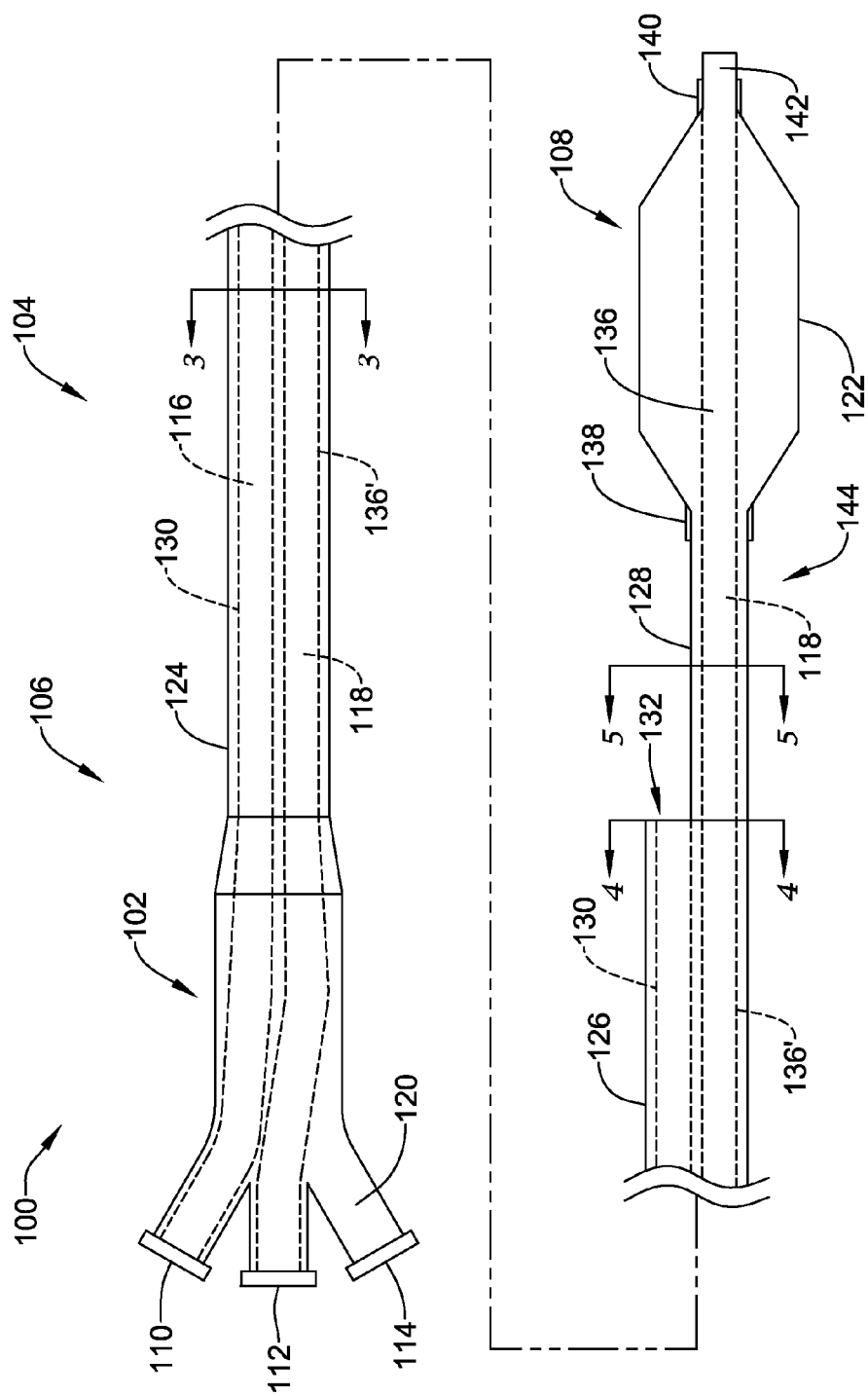
FIG. 1 is a schematic side view of an exemplary embodiment of a catheter.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification. All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

While the devices and methods described herein are discussed relative to treatment of occluded blood vessels or coronary arteries, it is contemplated that the devices and methods may be used in other applications as desired.

The term "proximate" refers to a relatively close physical distance, but does not have any bearing on distance to or from a user. For purposes of this disclosure, the term "proximal end" refers to the end closer to the device operator during use, and "distal end" refers to the end further from the device operator during use.

The present disclosure provides devices for treating occluded blood vessels, the heart, as well as other anatomical organs and structures, and methods for constructing the same. In particular, the disclosure discloses a medical device that may take the form of an angioplasty catheter having a catheter shaft. An inflatable balloon may be mounted proximate a distal end of the catheter shaft. The catheter shaft may include a proximal outer tubular member, an inner tubular member attached to the proximal outer tubular member, and a distal outer tubular member attached to the proximal outer tubular member. For efficient and sufficient flow of contrast fluid, the present disclosure provides a dedicated contrast fluid lumen defined by the inner tubular member. More particularly, the contrast fluid lumen may deliver the fluid into a blood vessel lumen at a port (a contrast fluid delivery port) proximate or near the inflatable balloon. The contrast fluid delivery port may be located on the catheter shaft proximate to or near the balloon such that the contrast fluid may be delivered to a target location. FIG. 1 is a side view of an exemplary catheter 100 for use in minimally invasive surgery. The exemplary catheter 100 includes a hub assembly 102 having a catheter shaft 104 extending distally from the hub assembly 102. The hub assembly 102 may be operably connected to a proximal end 106 of the catheter shaft 104, and may be configured to assist an operator to manipulate the catheter shaft 104.

As shown in FIG. 1, the hub assembly 102 may be at the proximal end 106 of the catheter shaft 104 and may include one or more ports such as a contrast port 110, through which contrast fluid may be supplied, a guidewire port 112 for inserting a guidewire into a guidewire lumen, and an inflation port 114 through which an inflation media may be supplied. Thus, the ports 110, 112, and 114, in the hub assembly 102 may provide access to lumens 116, 118, and 120 respectively, in the catheter shaft 104. At the proximal end 106, the hub assembly 102 may be fitted with connectors such as luer connections for easy attachment. In one embodiment, the hub assembly 102 may be injection molded with the catheter shaft 104.

The catheter shaft 104 is a generally long, flexible tubular construction that may be inserted into the body for a medical diagnosis and/or treatment. As shown in FIG. 1, the catheter shaft 104 may extend distally from the hub assembly 102 to a distal end 108. The catheter shaft 104 may include a lumen extending between the proximal end 106 and the distal end 108. At the distal end 108 region of the catheter shaft 104, a therapeutic device such as an inflatable balloon 122 may be mounted that radially surrounds around the catheter shaft 104. The balloon 122 may be secured to the catheter shaft 104 by any suitable manner, for example, using heating and/or pressure, or by the use of an adhesive.

The catheter shaft 104 may be formed of a plurality of tubular members. As shown, the catheter shaft 104 may include an outer tubular member 124 having a lumen extending therein. In one aspect, the outer tubular member 124 may include a proximal outer tubular member 126 and a distal outer tubular member 128, joined to the proximal outer tubular member 126 (which will be discussed in detail in conjunction with FIG. 2). Each of the proximal outer tubular member 126 and the distal outer tubular member 128 may define a lumen extending therein. The distal outer tubular member 128 may be joined to the proximal outer tubular member 126 at a joint 134 such that the lumen of the proximal outer tubular member 126 may be in fluid communication with the lumen of the distal outer tubular member 128. At the joint 134, a distal end 148 of the proximal outer tubular member 126, a distal end 150 of the inner tubular member 130 and a proximal end 146 of the distal outer tubular member 128 may be joined together and bonded.

The proximal outer tubular member 126 may include an inner tubular member 130 extending through the proximal outer tubular member 126. In the shown embodiment, the proximal outer tubular member 126 and the inner tubular member 130 may be separate members and may extend substantially parallel to each other. In such instances, the proximal outer member 126 may be coupled to the inner tubular member 130 by any suitable coupling mechanism such as molding, adhesive bonding, thermal bonding, or other known mechanisms. While in other embodiments, the inner tubular member 130 may be integrally formed with, fixedly secured to, or otherwise coupled to the proximal outer tubular member 126.

The inner tubular member 130 may define a contrast fluid lumen 116 attached to the hub assembly 102 with a luer connection. The contrast fluid lumen 116 may extend through the proximal outer tubular member 126 from the hub assembly 102 to a contrast fluid delivery port 132, located proximate the joint 134, and the contrast fluid delivery port 132 may be in communication with the contrast fluid lumen 116. The contrast fluid lumen 116 may exit out of the proximal outer tubular member 126 a short distance proximal to the distal end 108 of the catheter shaft 104, where the balloon 122 is attached. By this way, the contrast fluid lumen 116 may be configured to deliver the contrast fluid close to the balloon 122. As the contrast fluid is delivered close to the balloon 122, thus the amount of contrast fluid required to be injected into the blood vessel may be reduced.

The contrast port 110 at the proximal end 106 may be in fluid communication with the contrast fluid lumen 116. As is known, the contrast fluid helps an operator to observe the blood vessel by a medical radiography technique like fluoroscopy and is thus able to locate the stenosis to be treated. The contrast fluid may be an iodine based solution, for example, and it can be visualized using any known radiography instrument. Dispersion of the contrast fluid within the blood vessel allows the user to visualize the location of the stenosis and the effectiveness of the angioplasty procedure.

In FIG. 1, the contrast fluid may be injected into the contrast fluid lumen 116 by connecting a syringe, power injection machine or similar device to the contrast port 110 at the proximal end 106, and injecting fluid through the contrast fluid lumen 116 into the proximal inner tubular member 130 and delivered to the blood vessel through the contrast fluid delivery port 132. In other words, the contrast fluid introduced at the contrast port 110 traverses the length of the proximal inner tubular member 130 and may be injected close to the balloon 122 via the contrast fluid delivery port 132.

As seen from FIG. 1, length of the inner tubular member 130 may be equivalent to that of the proximal outer tubular member 126, but the thickness or diameter of the inner tubular member 130 may be less than the proximal outer tubular member 126. The inner tubular member 130 may be shaped and sized to be disposed within the proximal outer tubular member 126. The inner tubular member 130 may have a substantially uniform diameter or dimension throughout the length, or it may have a non-uniform cross-section in some implementations. For instance, the contrast fluid lumen 116 may have a tapered shaped that allows the appropriate injected contrast fluid flows from the hub assembly 102 to the lumen of the proximal inner tubular member 130 and consequently flows inside the patient's body (not shown). In one exemplary embodiment, an inner diameter of the contrast fluid lumen 116 may be 0.015 inches, for example.

A guidewire tube 136 may extend through the lumen of the outer tubular member 124 that defines a guidewire lumen 118. The guidewire lumen 118 may extend through at least a portion of the catheter shaft 104, but in the shown embodiment, the guidewire lumen 118 may extend from the hub assembly 102 to the distal end 108 of the catheter shaft 104. More particularly, the guidewire tube 136 may extend through the proximal outer tubular member 126, along an exterior of the inner tubular member 130 and within the lumen of the distal outer tubular member 128. At the proximal end 106 of the catheter shaft 104, the hub assembly 102 may include the guidewire port 112 in fluid communication with the guidewire lumen 118. To help the flexible catheter shaft 104 reach the target area, a guidewire (although not shown) may be temporarily disposed within the guidewire lumen 118. The guidewire may extend from the hub assembly 102 to a distal end 142 of the guidewire tube 136. As is known, the guidewire may be a metallic or polymeric wire and/or a stylet. In some embodiments, the guidewire may be made up of biocompatible materials such as stainless steel or nitinol.

The guidewire lumen 118 may be a hollow tubular structure that may allow passage of the guidewire through it and distally beyond the catheter shaft 104. The guidewire lumen 118 may be configured with any suitable shape such as circular, oval, polygonal, or irregular. The guidewire lumen 118 may have cross-sectional dimensions greater than the cross-sectional dimensions of the guidewire. In one example, the inner diameter of the guidewire tube 136 may be about 0.015 inches, for example.

As shown in FIG. 1, the inflation lumen 120 may extend through the catheter shaft 104 from the hub assembly 102 at the proximal end 106, to the balloon 122. The inflation lumen 120 may be defined by an inner surface of the outer tubular member 124, in particular, proximal outer tubular member 126, and an exterior surface of the guidewire tube 136 and an exterior surface of the inner tubular member 130. The inflation lumen 120 may extend from the proximal inflation port 114 through the catheter shaft 104 and terminates at an inflation lumen opening disposed within the balloon 122. The inflation lumen 120 may be used to inflate or deflate the balloon 122 with an inflation fluid, e.g., saline. The inflation lumen 120 may be in fluid communication with the inflation port 114 at the proximal end of the hub assembly 102 and the balloon 122 at the distal end of the catheter shaft 104 as shown.

In some embodiments, a fluid source such as a saline source may be coupled to the inflation port 114 of the hub assembly 102. The balloon 122 may be inflated by forcing fluid from the fluid source into the balloon 122 via the inflation lumen 120. The fluid introduced through the inflation port 114 may travel the length of the inflation lumen 116 and can be introduced into the balloon 122 to inflate the same.

As shown in FIG. 1, the balloon 122 may include a proximal waist 138 which may be secured to the distal end 144 of the distal outer tubular member 128 and a distal waist 140 of the inflatable balloon 122 may be secured to a distal end 142 of the guidewire tube 136.

The balloon 122 may be formed from polyurethane, silicone, PET (polyethylene terephthalate), polyamide, polyether block amide, and other suitable polymers known in the art. In one embodiment, the balloon 122 may be integrally formed onto the catheter shaft 104 adjacent to the distal end region/portion of the catheter shaft 104. Alternatively, the balloon 122 may be formed independent of the catheter shaft 104 by any process known in the art and then fixedly attached to the catheter shaft 104.

Although the illustrated embodiments employ the inflatable balloon 122, it should be understood that any therapeutic device, such as an expandable element could be employed as required. For example, a self-expanding basket or an ablation device could be useful in some situations.

In some embodiments, the catheter 100 may be configured as an over the wire (OTW) catheter, having the guidewire port 112 for inserting the guidewire into the guidewire lumen 118. In these embodiments, the guidewire lumen 118 may extend along essentially the entire length of catheter shaft 104. While in other embodiments, the catheter 100 may be configured as a single operator exchange (SOE) (monorail or rapid exchange) catheter, having a rapid exchange port (1102, see FIG. 11) located distal of the proximal end 106 of the catheter shaft 104 for inserting the guidewire into a guidewire lumen. As such, the guidewire lumen may extend over only a portion of the length of catheter shaft 104. Such embodiments may allow the catheter to be used with a shorter guidewire. It may be noted that in instances where the catheter is an SOE catheter, the hub assembly 102 may not include the port 112. Where the catheter is an OTW catheter, however, the rapid exchange port 1102 may be omitted. It is noted that other catheter constructions are contemplated.

In many embodiments, the distal end portion 108 of the catheter shaft 104 may be softer or more flexible than the proximal end portion 106 so the catheter shaft 104 may more easily navigate inside the patient's body. The cross-sectional dimensions of the catheter shaft 104 may vary according to the desired application, but they are generally smaller than the typical diameter of the blood vessel lumen in locations where the catheter 100 may be used, such as in a coronary or peripheral artery.

In some embodiments, the tubular members—proximal outer member 126, distal outer member 128, inner tubular member 130, and guidewire tube 136 may be configured with a substantially circular cross-section. Other suitable cross-sectional shapes may be elliptical, oval, polygonal, or irregular. The cross-sectional dimensions and/or length of the tubular members 126, 128, 130, 136 may vary according to the desired application.

The tubular members (proximal outer tubular member 126, inner tubular member 130, distal outer tubular member 128, and guidewire tube 136) of the catheter shaft 104 may be formed from any suitable biocompatible material, such as suitable polymers. The members 126, 128, 130, 136 may be formed from the same material, or different materials may be employed for their various characteristics. In general, suitable polymeric materials may include, for example, polyamide, PEBAX® (polyether block amide), polyurethane, polyethylene, nylon, and polyethylene terepthalate. Alternatively, a combination of polymeric and metallic materials may be employed as well. A suitable combination material may be a polymeric material reinforced with metallic wires, a braid and/or a coil to increase rigidity of a portion of the catheter shaft. In some instances, one or more of the tubular members 126, 128, 130, 136 may be formed of a metallic material, such as a nitinol or stainless steel hypotube. Furthermore, the catheter shaft 104, or a various members 126, 128, 130, 136 thereof, may be coated with a suitable low-friction material, such as polytetrafluoroethylene (PTFE), such as TEFLON®, polyetheretherketone (PEEK), polyimide, nylon, polyethylene, or other lubricious polymer coatings to reduce friction.

The catheter 100 as shown may be generally referred to as an angioplasty catheter, although use of the catheter 100 for stent placement or valve placement, or as another therapeutic catheter is contemplated. Those of skill in the art will appreciate that methods and devices in accordance with the present invention may be used to fabricate other types of catheter.

Figure 2:
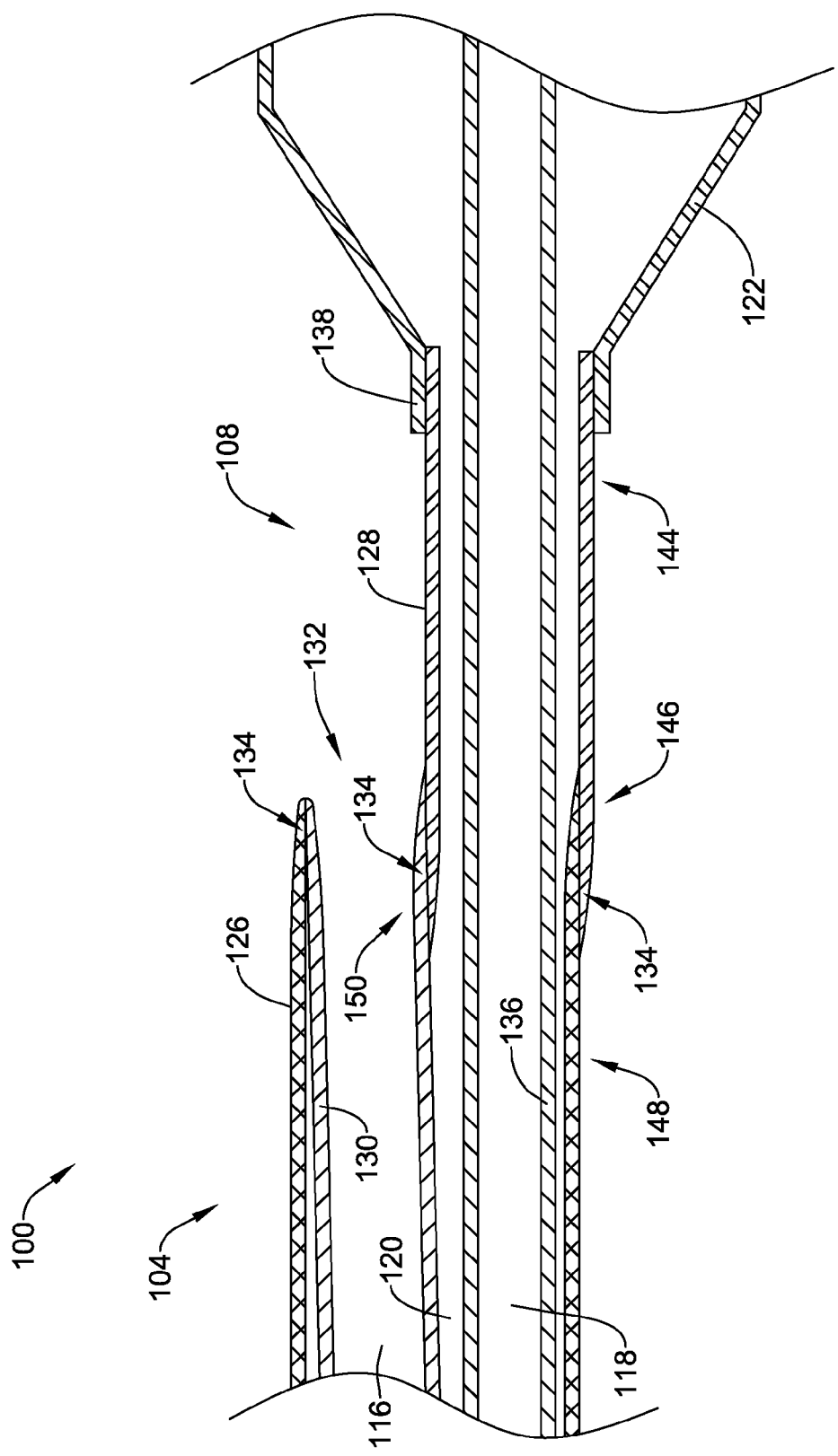
FIG. 2 is a cross-sectional side view of the exemplary catheter, showing bonding between various tubular members.

FIG. 2 shows a cross-sectional view of the catheter shaft 104 showing the joint 134. As discussed above, the catheter shaft 104 includes the proximal outer tubular member 126, the inner tubular member 130 and the distal outer tubular member 128 joined together at the joint 134. A distal end 148 of the proximal outer tubular member 126, a distal end 150 of the inner tubular member 130 and a proximal end 146 of the distal outer tubular member 128 may be joined together and bonded at the joint 134. These tubular members 126, 128, 130 may be bonded such that the lumen of the proximal outer tubular member 126 may be in fluid communication with the lumen of the distal outer tubular member 128. At the joint 134, the inner tubular member 130 may end and the contrast fluid delivery port 132 may open for effective delivery of fluid close to the balloon 122. The contrast fluid delivery port 132 may be in fluid communication with the contrast fluid lumen 116 such that contrast fluid may exit out of the distal end of the contrast fluid lumen 116 much closer to distal end 108 of the catheter shaft 104, where the balloon 122 is coupled.

Various bonding mechanisms including adhesive bonding or thermal bonding, for example may be used for bonding the tubular members together. In some embodiments, the proximal outer tubular member 126, or a portion thereof may be a metallic hypotube. The distal outer tubular member 128 may be fitted over, fitted within, or abut the proximal outer tubular member 126. These are examples, as any suitable arrangement may be utilized.

The guidewire tube 136 defines the guidewire lumen 118 through which the guidewire may be passed. As seen from FIG. 2, the guidewire tube 136 may extend through a portion of the proximal outer tubular member 126 proximal of the joint 134 and may extend through a portion of the distal outer tubular member 128 distal of the joint 134. Further, the distal end 144 of the distal outer tubular member 128 may be joined to the proximal waist 138 of the balloon 122, whereas the distal waist 140 of the balloon 122 may be bonded to the distal end 142 of the guidewire tube (although not shown in FIG. 2).

Figure 4:
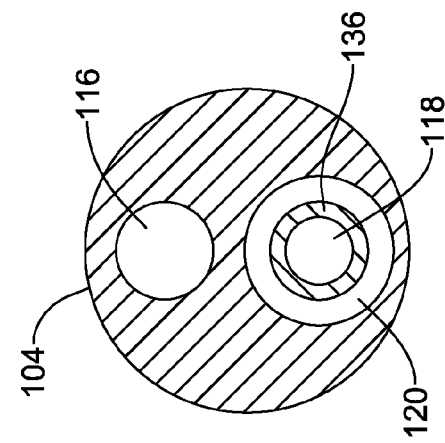
FIG. 4 is a cross-sectional view of the catheter shaft of the catheter of FIG. 1, taken along the plane 4-4 as shown in FIG. 1.
Figure 5:
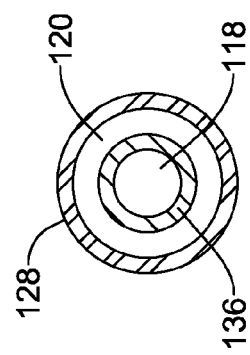
FIG. 5 is a cross-sectional view of the catheter shaft of the catheter of FIG. 1, taken along the plane 5-5 as shown in FIG. 1.
Figure 3:
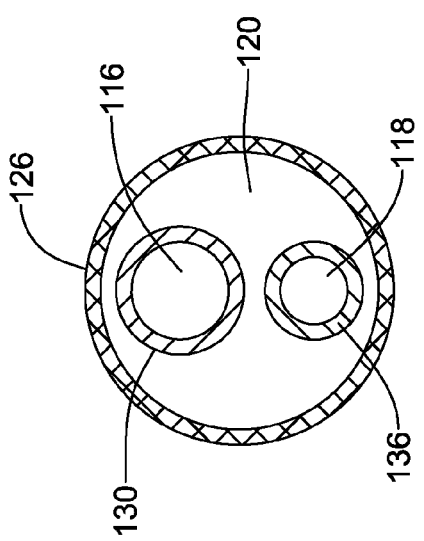
FIG. 3 is a cross-sectional view of the catheter shaft of the catheter of FIG. 1 taken along the plane 3-3 as shown in FIG. 1.

FIGS. 3-5 depict a cross-section of the catheter shaft 104 of FIG. 1 at different points along its length.

FIG. 3 is a cross-section of the proximal end region of the proximal outer tubular member 126 shown in FIG. 1 taken along the 3-3 plane. In the shown embodiment, the proximal outer tubular member 126 may be a hollow structure. Within the proximal outer tubular member 126, the inner tubular member 130 may be disposed that defines the contrast fluid lumen 116. The contrast fluid lumen 116 may extend through the proximal outer tubular member 126 and may be configured to deliver the contrast fluid. The guidewire tube 136 may extend through the proximal outer tubular member 126 along an exterior of the inner tubular member 130 in a side-by-side manner. The guidewire tube 136 may define the guidewire lumen 118 through which the guidewire (although not shown) may passed. The inflation lumen 116 may be defined between an inner surface of the proximal outer tubular member 126 and an exterior surface of the guidewire tube 136 and an exterior surface of the inner tubular member 130. For the current embodiment, the proximal outer tubular member 126 and the inner tubular member 130 are separate tubular structures.

FIG. 4 is a cross-sectional view of the catheter shaft 104 at the contrast fluid port 132, taken across the plane 4-4. In the shown embodiment, as a consequence of the joining process at the joint 134 as the proximal outer tubular member 126, the distal outer tubular member 128 and the inner tubular member 130 may be melded together. The guidewire tube 136 may extend through the lumen forming the inflation lumen 120 between the proximal outer tubular member 126 and the distal outer tubular member 128.

FIG. 5 is a cross-sectional view of a portion of the distal outer tubular member 128, along the 5-5 plane, as shown in FIG. 1. A portion of the guidewire tube 136 may extend within the distal outer tubular member 128, defining the guidewire lumen 118. As shown, the inflation lumen 120 may be defined between an inner surface of the distal outer tubular member 128 an exterior surface of the guidewire tube 136. However, it is understood that the inflation lumen 120 may be formed from a separate tubular structure, in other instances.

FIGS. 6-10 illustrate some steps of an exemplary method for constructing the catheter 100 and/or catheter shaft 104.

Figure 6:
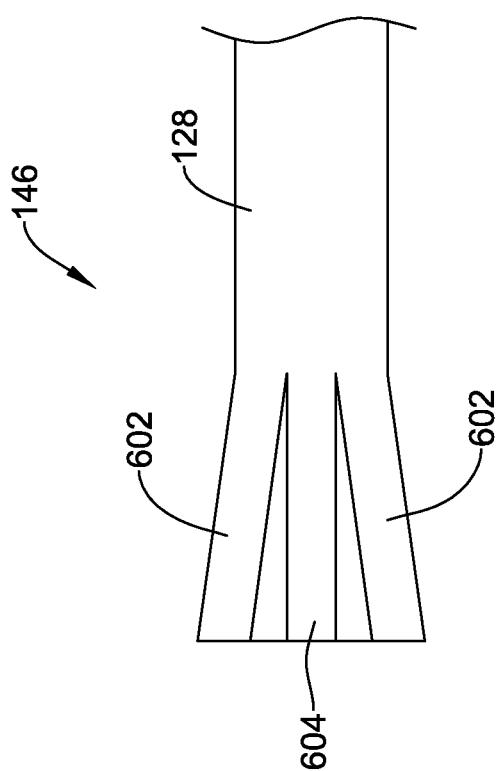
FIG. 6-FIG. 10 depict aspects of an exemplary method for constructing the catheter, according to one embodiment of the disclosure.

FIG. 6 is a side view of a proximal portion of the distal outer tubular member 128 prior to joining. Here it can be seen that the proximal end 146 of the distal outer tubular member 128 may be flared or otherwise enlarged, marked as 602. In addition, a pair of cuts, such as parallel cuts, may be formed in proximal end 146 of the distal outer tubular member 128 to define a tab 604. The tab 604 or tongue may be formed by cutting using any suitable cutting tool. The cuts may be formed from the proximal end 146 of the distal outer tubular member 128 to a few millimeters and the rest of the circumference of the proximal end 146 may be flared out into a cone shaped as depicted here.

Figure 7:
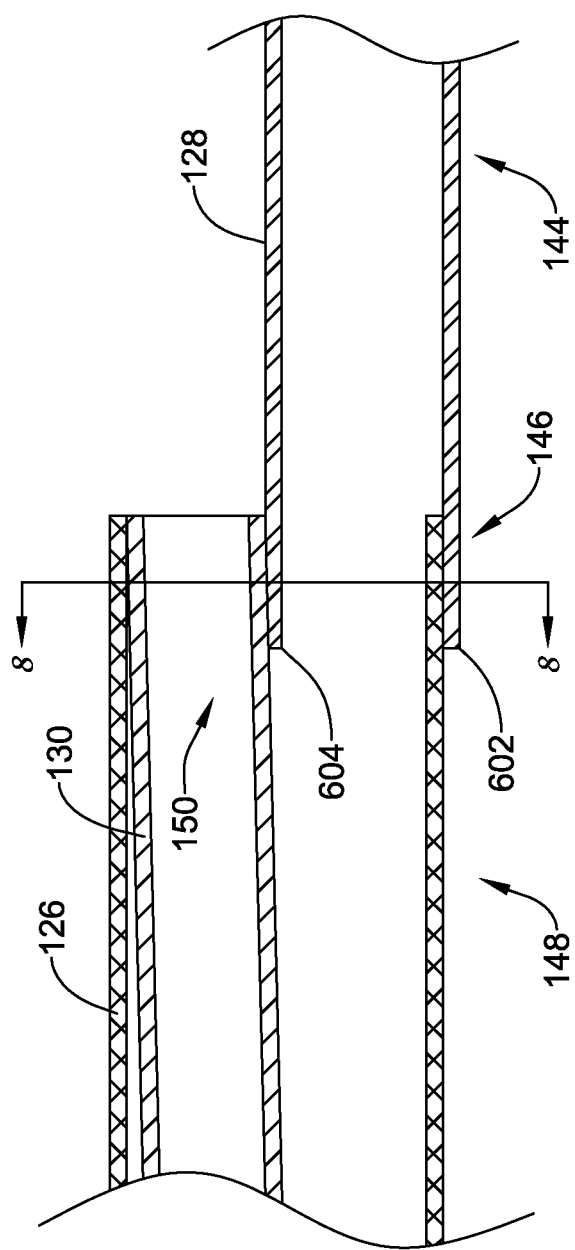

FIG. 7 shows an arrangement of the tubular members prior to bonding the tubular members together. The inner tubular member 130 may be inserted into the proximal outer tubular member 126. The tab 604 of the distal outer tubular member 128 may be positioned underneath the distal end 150 of the inner tubular member 130 (e.g., along an exterior portion of the inner tubular member 130) and may be inserted into the lumen of the proximal outer member 126, while the flared portion 602 of distal outer tubular member 128 may extend around the outside or surround an exterior of the proximal outer tubular member 126 as shown in FIG. 7. The contrast fluid lumen 116 may extend between the proximal outer tubular member 126 and distal outer tubular member 128.

Figure 8:
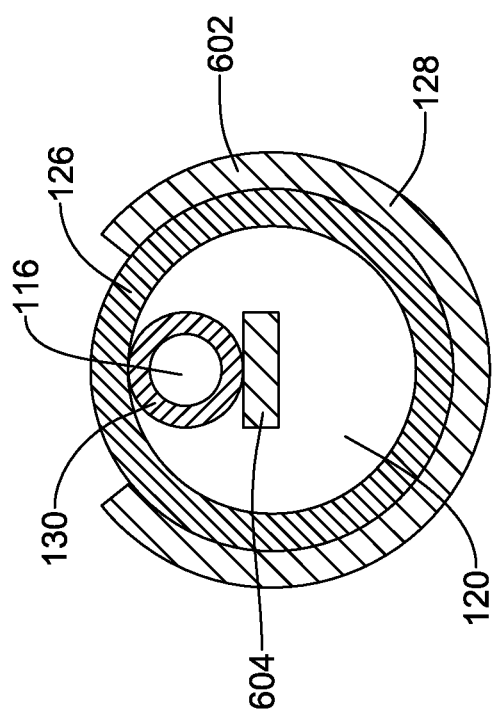

FIG. 8 shows the cross-sectional view of the above described arrangement taken along plane 8-8 of FIG. 7. In FIG. 8, the flared portion 602 of the distal outer tubular member 128 is shown to be disposed about the proximal outer tubular member 126; whereas the tab portion 604 of the distal outer tubular member 128 may sit beneath the inner tubular member 130 and within the lumen of the proximal outer tubular member 126. The contrast fluid lumen 116 defined by the inner tubular member 130 is also shown in FIG. 8.

Figure 9:
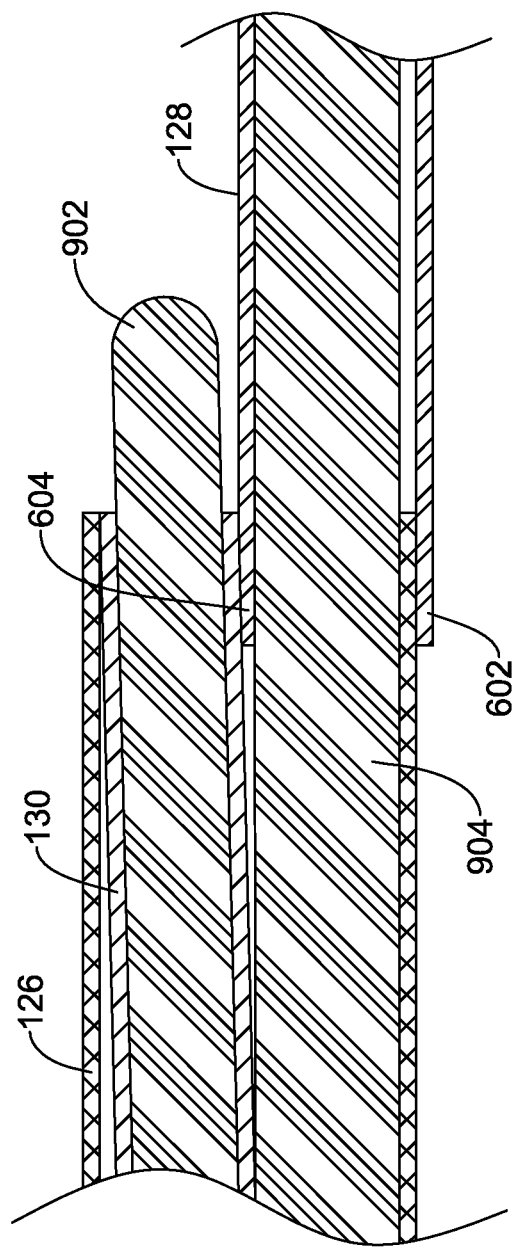
Figure 10:
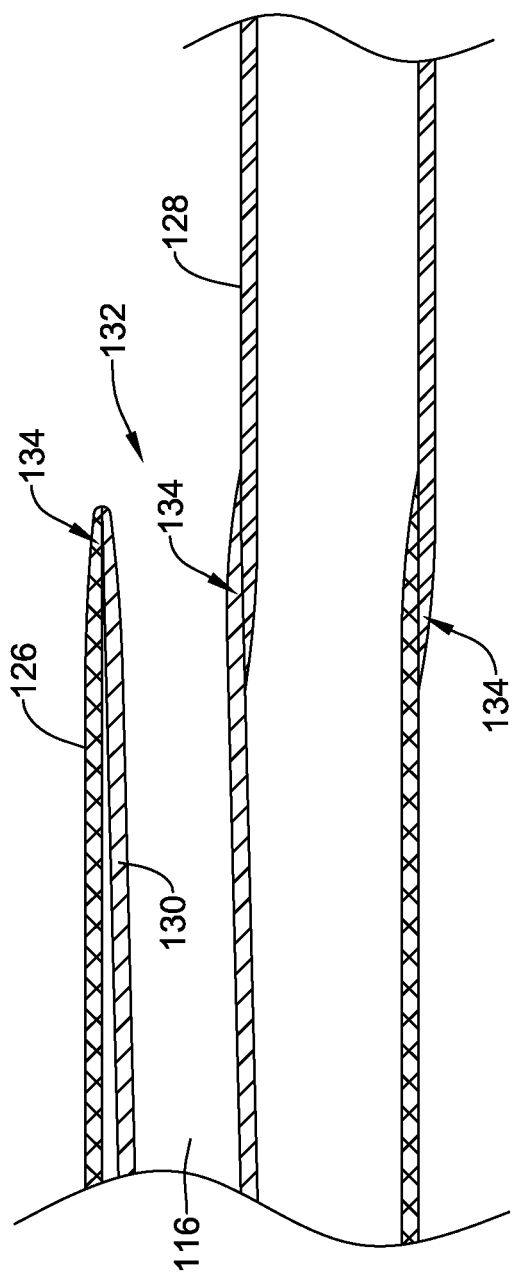

FIG. 9 shows an arrangement for constructing the catheter 100. As shown, a first mandrel 902 may be inserted within the inner tubular member 130 disposed within the lumen of the proximal outer tubular member 126. A second mandrel 904 may be disposed between the proximal outer tubular member 126 and the distal outer tubular member 128. The mandrels 902 and 904 may be appropriately shaped to form the lumens of the inner tubular member 130 and the proximal outer tubular member 126 and distal outer tubular member 128. After the mandrels 902 and 904 are inserted, heat and pressure may be applied to the assembly and may be melted together to bond shaft components together, thereby creating the joint 134. Heat may be applied using laser or other thermal process as known in the art. Once the joint 134 is created, the mandrels 902 and 904 can be removed and the configuration shown in FIG. 10 is the result.

After the joint 134 is formed, the guidewire tube 136 may be inserted through the lumen extending between the proximal outer tubular member 126 and the distal outer tubular member 128, through which the guidewire may be inserted. The contrast fluid lumen 116 may be formed by the inner tubular member 130 and space between the guidewire tube 136, and proximal and distal outer tubular members 126, 128, may define the inflation lumen 120.

Figure 11:
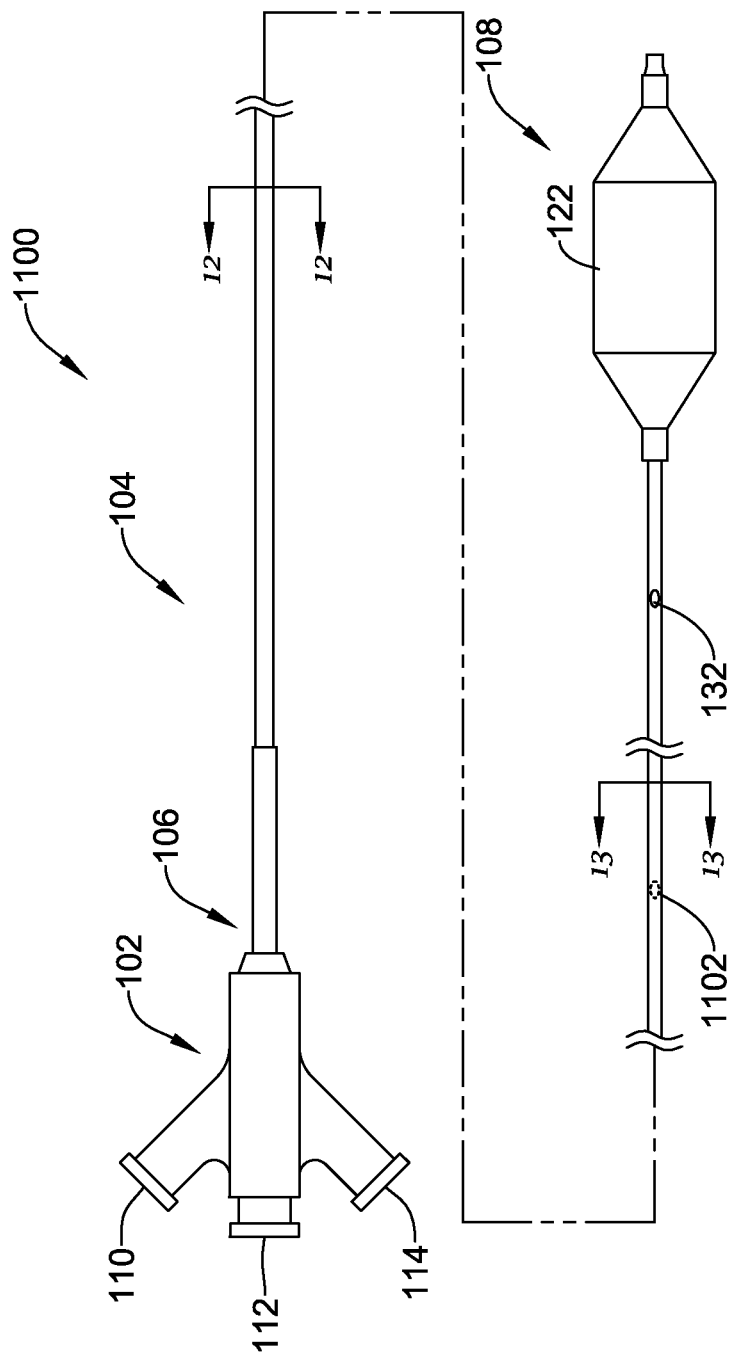
FIG. 11 is a schematic side view depicting another exemplary embodiment of a catheter.

FIG. 11 is a plan view of an exemplary embodiment of a catheter 1100—for example, an over-the-wire (OTW) catheter, illustrating the hub assembly 102 and the catheter shaft 104 extending distally from the hub assembly 102 to the distal end 108. Some structural and functional details of the hub assembly 102 and the catheter shaft 104 have already been discussed in conjunction with FIG. 1.

The hub assembly 102 of the catheter 1100 may include a contrast fluid port 110 in fluid communication with a contrast fluid lumen 1202, an inflation port 114 in fluid communication with the balloon 122 via an inflation lumen 1204, and a guidewire port 112 in communication with the guidewire lumen 118 extending through the length of the catheter shaft 104.

In other instances, the catheter 1100 may be a rapid exchange catheter, including a guidewire port 1102 (shown in phantom lines) defined at a distal end portion 108 of the catheter shaft 104, providing access to the guidewire lumen 118. Thus, the guidewire tube 136 defining the guidewire lumen 118 may not extend to the hub assembly 102 at the proximal end 106 of the catheter shaft 104, but rather, may terminate at the guidewire port 1102. In such instances, a guidewire (although not shown) may exit at a point along the shaft 104 in the distal end portion 108. As it can be seen, the guidewire port 1102 may be formed proximal or distal to the contrast fluid delivery port 132 and distal of the hub assembly 102, although other locations may be contemplated. The guidewire port 1102 may be formed by a process as known in the art.

Figure 12B:
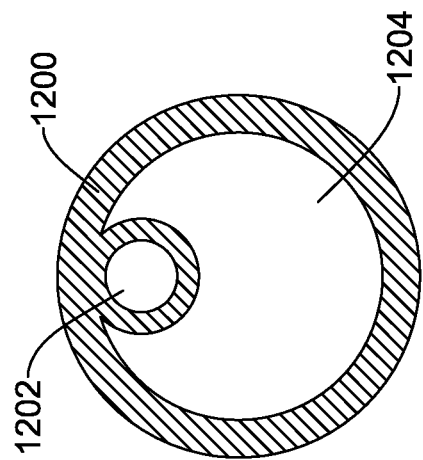
FIG. 12B is an alternative cross-sectional view of the catheter shaft of the catheter of FIG. 11, taken along the plane 12-12 as shown in FIG. 11.
Figure 12A:
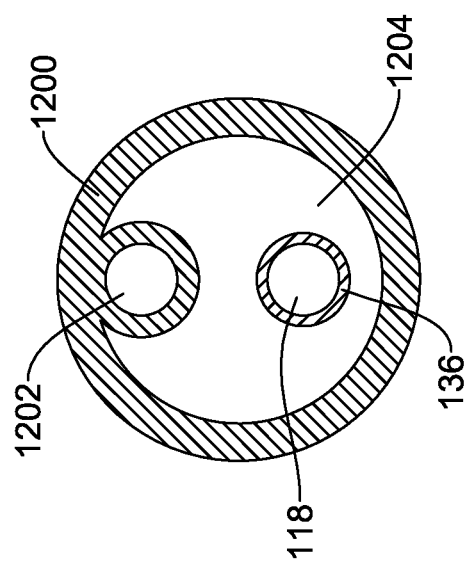
FIG. 12A is an exemplary cross-sectional view of the catheter shaft of the catheter of FIG. 11, taken along the plane 12-12 as shown in FIG. 11.

FIG. 12A is a cross-sectional view of the catheter shaft 104 of the catheter 1100 shown in FIG. 11, taken along the plane 12-12. In the shown embodiment, the outer tubular member 1200 may be a hollow cross-section. A contrast fluid lumen 1202 may be extruded with the outer tubular member 1200. As it can be seen, the contrast fluid lumen 1202 may be formed as a portion of the outer tubular member 1200, such as a coextruded portion of the outer tubular member 1200. The guidewire tube 136 may be disposed through the outer tubular member 1200 external of the contrast fluid lumen 1202 and may extend from the hub assembly 102 through the balloon 112 to the distal end of the catheter 1100. The inflation lumen 1204 may be defined by the space exterior to the contrast fluid lumen 1202 and the guidewire tube 136 defining the guidewire lumen 118.

FIG. 12B is an alternative cross-sectional view of the catheter shaft 104 of the catheter 1100 shown in FIG. 11, taken along the plane 12-12 in instances in which the catheter 1100 is a rapid exchange catheter. In such an embodiment, the proximal end portion of the outer tubular member 1200 (e.g., proximal of the guidewire port 1102) may not include the guidewire tube 136, as guidewire tube 136 may extend from the distal end of the catheter and terminate at the guidewire port 1102.

Figure 13:
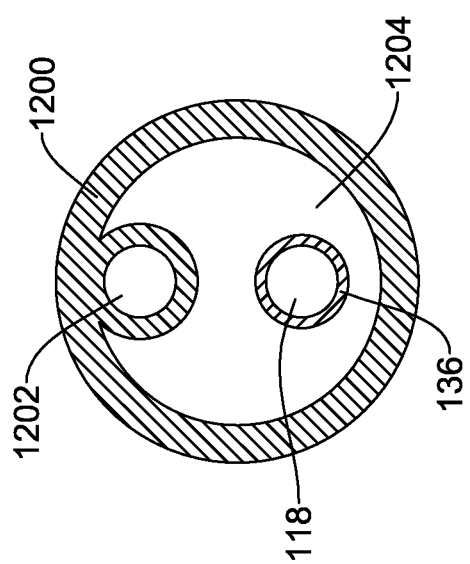
FIG. 13 is an exemplary cross-sectional view of the catheter shaft of the catheter of FIG. 11, taken along the plane 13-13 as shown in FIG. 11.

FIG. 13 is a cross-sectional view of the catheter shaft 104 of the catheter 1100 of FIG. 11, along the plane 13-13. As noted above, in this embodiment, the contrast fluid lumen 1202 may be formed by a co-extrusion process. The guidewire tube 136 may be disposed within a lumen of the outer tubular member 1200, defining the guidewire lumen 118. The guidewire lumen 118 may extend distally through which a guidewire may pass. The inflation lumen 1204 may be defined by all the space not taken up by the contrast fluid lumen 1202 or the guidewire tube 136.

In an embodiment such as that shown in FIG. 11 where the contrast fluid lumen 1202 may be coextruded with the outer tubular member 1200, the contrast fluid delivery port 132 may be formed by creating (e.g., punching, machining, drilling, etc.) a hole through the tubular wall of the outer tubular member 1200 into the contrast fluid lumen 1202 at a desired location proximate the balloon 122, for example.

In one exemplary embodiment, a method of constructing a medical catheter is disclosed. The method may include bonding an end (i.e. the distal end) of the proximal outer tubular member, an end (i.e. proximal end) of the distal outer tubular member and an end (i.e., distal end) of the inner tubular member together at the joint such that the lumen of the proximal outer tubular member is in communication with a lumen of the distal outer tubular member. The method may further include forming a port at the joint in communication with the lumen of the inner tubular member. The method may further include positioning the guidewire tube across the joint such that the first portion of the guidewire tube is positioned within the lumen of the proximal outer tubular member and the second portion of the guidewire tube is positioned within the lumen of the distal outer tubular member. The space between the exterior surface of the guidewire tube and the interior surface of the proximal and distal outer tubular members defines an inflation lumen in communication with the inflatable balloon. Moreover, the method may include bonding the proximal waist of an inflatable balloon to the distal outer tubular member, and bonding the distal waist of the inflatable balloon to the guidewire tube.

The present disclosure discloses a dedicated contrast fluid lumen configured for contrast flow, providing better performance for catheters requiring visualization using contrast fluid, and this also may reduce the amount of contrast needed for visualization. The contrast fluid lumen may be incorporated in a catheter—an angioplasty catheter for example, thereby permitting the catheter to have a greater outer diameter while allowing for sufficient contrast flow rate and sufficient space for navigation in a guide catheter. Further, the contrast fluid may exit closer to the point of interest in the anatomy reducing loss to side branches, and providing more focused visualization. Additionally, the disclosure may permit the use of smaller sizes of the guide catheter, as no space is required between the inside of the guide catheter and outside of the angioplasty catheter, for contrast fluid delivery.

It is understood that aspects of the present disclosure may be utilized in various types of catheters including in hypertension catheter shafts requiring large lumens for flow, large balloon catheters requiring large lumens for faster inflation or deflation, kink-prone catheters (which may be supported by the dedicated contrast fluid lumen), and peripheral catheters that extend a large distance distally out of the guide catheter.

Those skilled in the art will recognize the aspects of the present disclosure may be manifest in a variety of forms other than the specific embodiments described and contemplated herein. Accordingly, departure in form and detail may be made without departing from the scope and spirit of the present disclosure as described in the appended claims.

What is claimed is:

1. A catheter comprising:
   a hub assembly;
   a catheter shaft extending distally from the hub assembly to a distal end;
   an inflatable balloon mounted proximate the distal end of the catheter shaft;
   an inflation lumen extending through the catheter shaft from the hub assembly to the inflatable balloon;
   a guidewire lumen extending through at least a portion of the catheter shaft; and
   a contrast fluid lumen extending through the catheter shaft to a contrast fluid delivery port located proximate the inflatable balloon, the contrast fluid lumen configured to deliver contrast fluid to a target location;
   wherein the catheter shaft includes an outer tubular member having a lumen extending therethrough, and a guidewire tube extending through the lumen of the outer tubular member, the outer tubular member includes a proximal outer tubular member and a distal outer tubular member joined to the proximal outer tubular member at a joint;
   wherein the inflation lumen is defined between an inner surface of the outer tubular member and an outer surface of the guidewire tube; and
   wherein the guidewire lumen is defined by the guidewire tube.

2. The catheter of claim 1, wherein the contrast fluid lumen is defined by an inner tubular member extending through the outer tubular member.

3. The catheter of claim 2, wherein the inner tubular member extends along an exterior of the guidewire tube.

4. The catheter of claim 1, wherein the contrast fluid delivery port is located at the joint.

5. The catheter of claim 4, wherein the contrast fluid lumen is defined by an inner tubular member extending through the outer tubular member from the hub assembly to the contrast fluid delivery port.

6. The catheter of claim 5, wherein a distal end of the proximal outer tubular member, a proximal end of the distal outer tubular member and a distal end of the inner tubular member are bonded together at the joint.

7. The catheter of claim 6, wherein the guidewire tube extends through a portion of the proximal outer tubular member proximal of the joint and extends through a portion of the distal outer tubular member distal of the joint.

8. The catheter of claim 1, wherein the contrast fluid lumen is coextruded with the outer tubular member.

9. The catheter of claim 1, wherein the hub assembly includes a guidewire port in communication with the guidewire lumen, a contrast fluid port in fluid communication with the contrast fluid lumen, and an inflation port in fluid communication with the inflation lumen.

10. A catheter comprising:
a hub assembly;
a catheter shaft extending distally from the hub assembly, the catheter shaft including a proximal outer tubular member, a distal outer tubular member, an inner tubular member extending through the proximal outer tubular member, and a guidewire tube extending through the distal outer tubular member;
a therapeutic device mounted on a distal end region of the catheter shaft; and
a contrast fluid delivery port located on the catheter shaft proximal of the therapeutic device for delivering a contrast fluid to a target location;
wherein a distal end of the proximal outer tubular member, a proximal end of the distal outer tubular member and a distal end of the inner tubular member are bonded together at a joint;
wherein the contrast fluid delivery port is located proximate the joint.

11. The catheter of claim 10, wherein the inner tubular member defines a contrast fluid delivery lumen extending from the hub assembly to the contrast fluid delivery port.

12. The catheter of claim 11, wherein the guidewire tube extends through the proximal outer tubular member along an exterior of the inner tubular member in a side-by-side manner.

13. The catheter of claim 12, wherein the guidewire tube extends to the hub assembly.

14. The catheter of claim 10, wherein the therapeutic device is an inflatable balloon.

15. The catheter of claim 14, wherein a proximal waist of the inflatable balloon is secured to a distal end of the distal outer tubular member and a distal waist of the inflatable balloon is secured to a distal end of the guidewire tube.

16. A method of constructing a medical catheter, comprising:
bonding an end of a proximal outer tubular member, an end of a distal outer tubular member and an end of an inner tubular member together at a joint such that a lumen of the proximal outer tubular member is in communication with a lumen of the distal outer tubular member;
forming a port at the joint in communication with a lumen of the inner tubular member; and
positioning a guidewire tube across the joint such that a first portion of the guidewire tube is positioned within the lumen of the proximal outer tubular member and a second portion of the guidewire tube is positioned within the lumen of the distal outer tubular member.

17. The method of claim 16, further comprising:
bonding a proximal waist of an inflatable balloon to the distal outer tubular member; and
bonding a distal waist of the inflatable balloon to the guidewire tube.

18. The method of claim 17, wherein a space between an exterior surface of the guidewire tube and an interior surface of the proximal and distal outer tubular members defines an inflation lumen in communication with the inflatable balloon.

* * * * *